(12) United States Patent
Chen et al.

(10) Patent No.: US 8,410,305 B2
(45) Date of Patent: Apr. 2, 2013

(54) INTERMEDIATES AND METHODS FOR THE PREPARATION OF EPOTHILONES

(75) Inventors: Yue Chen, Tianjin (CN); Yong Li, Palo Alto, CA (US)

(73) Assignee: Kosan Biosciences Incorporated, Hayward, CA (US)

( * ) Notice: Subject to any disclaimer, the term of this patent is extended or adjusted under 35 U.S.C. 154(b) by 343 days.

(21) Appl. No.: 12/741,757

(22) PCT Filed: Nov. 12, 2008

(86) PCT No.: PCT/US2008/083259
§ 371 (c)(1),
(2), (4) Date: May 6, 2010

(87) PCT Pub. No.: WO2009/064800
PCT Pub. Date: May 22, 2009

(65) Prior Publication Data
US 2010/0267943 A1    Oct. 21, 2010

Related U.S. Application Data

(60) Provisional application No. 60/987,282, filed on Nov. 12, 2007.

(51) Int. Cl.
*C07C 69/66*    (2006.01)
*C07C 233/00*    (2006.01)

(52) U.S. Cl. ......... 560/183; 560/179; 564/204; 564/205

(58) Field of Classification Search .................. None
See application file for complete search history.

(56) References Cited

U.S. PATENT DOCUMENTS 6,893,859 B2    5/2005    Ashley et al.
2002/0165415 A1    11/2002    Georg et al.

OTHER PUBLICATIONS

Zhao et al., Tetrahedron (2007); vol. 63, pp. 8774-8780.*
Harris et al., Journal of Organic Chemistry (1999); vol. 64, pp. 8434-8456.*
Rivken et al., Journal of American Chemical Society (2004); vol. 126, pp. 10913-10922.*
International Search Report and Written Opinion issued for PCT/US08/83259 on Feb. 2, 2009.
Rivken et al., "Discovery of (E)-9, 10-Dehydroepothilones through Chemical Synthesis: On the Emergence of 26-Trifluoro-(E)-9, 10-dehydro-12, 13-desoxyepothilone B as a Promising Anticancer Drug Candidate,"; Journal of American Chemical Society (2004); vol. 126, pp. 10913-10922.
Harris et al., "Complex Target-Oriented Synthesis in the Drug Discovery Process: A Case History in the dEpoB Series," Journal of Organic Chemistry (1999); vol. 64, pp. 8434-8456.
Zhao et al., "Reactions of alanes and aluminates with tri-substituted epoxides. Development of a stereospecific alkynylation at the more hindered carbon,"; Tetrahedron (2007); vol. 63, pp. 8774-8780.

* cited by examiner

*Primary Examiner* — Karl J Puttlitz
(74) *Attorney, Agent, or Firm* — Fox Rothschild LLP; Gerard P. Norton; W. Jerry Liu

(57) ABSTRACT

Highly efficient methods are provided for preparing key intermediates in the synthesis of epothilones and use new alane reagents which are broadly applicable and can provide selected components having a variety of substituents groups.

4 Claims, 2 Drawing Sheets

Scheme 1

INTERMEDIATES AND METHODS FOR THE PREPARATION OF EPOTHILONES

CROSS REFERENCE TO RELATED APPLICATIONS

This application is a 371 National Phase Application of PCT/US08/83259 filed Nov. 12, 2008. PCT/US08/83259 claims the benefit of U.S. Provisional Application Ser. No. 60/987,282 filed on Nov. 12, 2007, both applications are which is incorporated herein by reference.

BACKGROUND OF THE INVENTION

The class of polyketides known as epothilones has emerged as a source of potentially therapeutic compounds having modes of action similar to paclitaxel. Interest in the epothilones and epothilone analogs has grown with the observations that certain epothilones are active against tumors that have developed resistance to paclitaxel as well as a reduced potential for undesirable side-effects. Among the epothilones and epothilone analogs being investigated for therapeutic efficacy are the natural product epothilone B, the semi-synthetic epothilone B derivative BMS-247550, also known as ixabepilone, and the synthetic analog EPO-ZK.

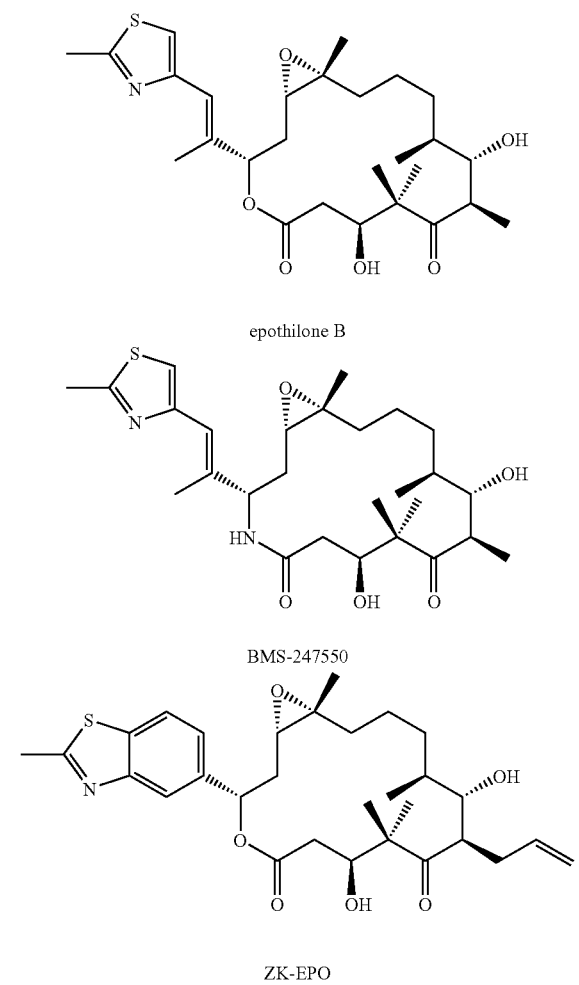

Desoxyepothilone B, also known as "epothilone D" is another epothilone derivative having promising anti-tumor properties that is being investigated for therapeutic efficacy. This compound has demonstrated lower toxicity than epothilones having 12,13-epoxides.

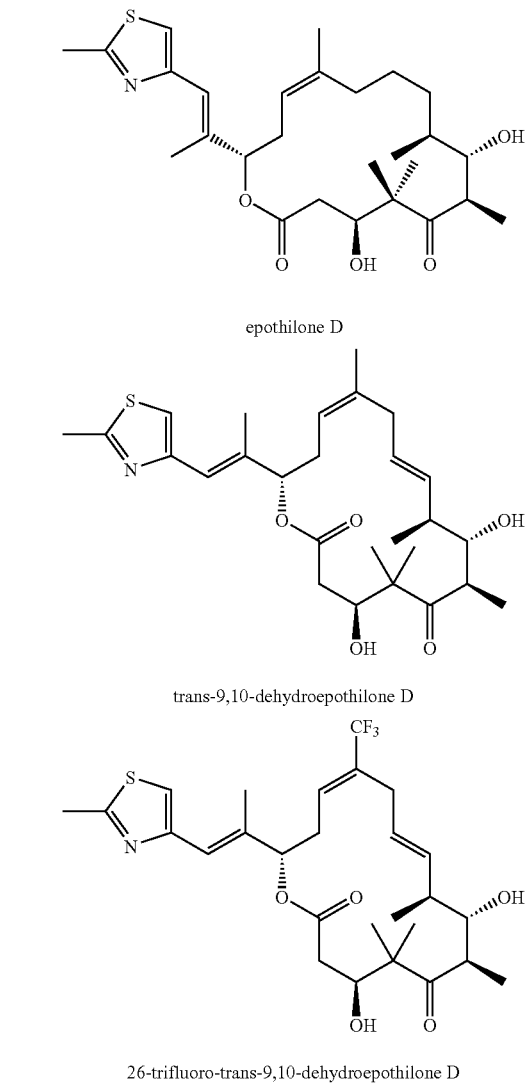

More recently analogs of epothilone D having greater in vitro potency have been described, including trans-9,10-dehydroepothilone D ((4S,7R,8S,9S,10E,13Z,16S)-4,8-dihydroxy-5,5,7,9,13-pentamethyl-16-[(1E)-1-methyl-2-(2-methyl-4-thiazolyl)ethenyl]-oxacyclohexadeca-10,13-diene-2,6-dione) and its 26-trifluoro-analog, also known as fludelone. These compounds demonstrate remarkable antitumor activity in mouse xenograft models (Rivkin et al., "Discovery of (E)-9,10-dehydroepothilones through Chemical Synthesis: On the Emergence of 26-Trifluoro-(E)-9,10-dehydro-12,13-desoxyepothilone B as a Promising Anticancer Drug Candidate," *J. Am. Chem. Soc.* 126: 10913-10922 (2004).

Although various methods for preparing epothilone derivatives and analogs having anti-tumor activity have been disclosed in the art, including fermentation, semi-synthesis, and total chemical synthesis, there is continuing unmet need for new, more efficient methods for preparing these promising anticancer agents.

BRIEF SUMMARY OF THE INVENTION

In one aspect, the present invention provides compounds, useful as intermediates in the preparation of epothilones, the compounds having the formula:

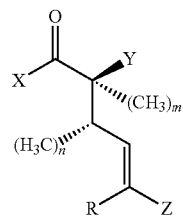

I wherein the subscripts n and m are each independently 0 or 1, indicating the absence or presence of methyl groups at the respective positions. The letter X represents a member selected from $CH_3$, $OR^1$, $NHR^2$ and $N(R^2)OR^1$; wherein $R^1$ is selected from H, lower alkyl, a carboxylic acid protecting group and a hydroxy protecting group, and $R^2$ is selected from H, lower alkyl and an amino protecting group. The letter Y represents a member selected from $OR^3$ and $N(R^4)_2$, wherein $R^3$ is selected from H, lower alkyl and a hydroxy protecting group, and each $R^4$ is independently selected from H, lower alkyl and an amino protecting group. The letter Z represents a member selected from $CH_3$ and $CF_3$. The letter R represents a member selected from vinyl, allyl, 2-buten-1-yl and 3-trimethylsilylprop-2-yn-1-yl. In the compounds above, (a) when X is $CH_3$, Y is other than OH;
(b) when X is $N(CH_3)OCH_3$, and Z is $CF_3$, then Y is other than OH; and
(c) when X is $N(CH_3)OCH_3$, and Z is $CH_3$, then Y is other than O—Si$(Et)_3$.

Additionally, the compounds above are substantially free of their enantiomeric or diastereomeric forms.

In another aspect, the present invention provides alane reagents, comprising one or more compounds having the formula:

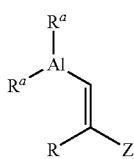

wherein each $R^a$ is independently selected from lower alkyl and cycloalkyl; R is a member selected from vinyl, allyl, 2-buten-1-yl and 3-trimethylsilylprop-2-yn-1-yl; and Z is a member selected from $CH_3$ and $CF_3$.

In yet another aspect, the present invention provides method for the preparation of an epothilone intermediate, the method comprising:

a) contacting a compound having the formula:

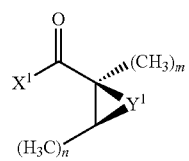

wherein the subscripts n and m are each independently 0 or 1, indicating the absence or presence of methyl groups at the respective positions; $X^1$ is a member selected from $OR^1$, $N(R^2)_2$ and $N(R^2)OR^1$; wherein $R^1$ is selected from H, lower alkyl, a carboxylic acid protecting group and a hydroxy protecting group, and each $R^2$ is independently selected from H, lower alkyl and an amino protecting group; $Y^1$ is a member selected from O and $NR^4$, wherein $R^4$ is selected from the group consisting of H, lower alkyl and an amino protecting group; with an alane reagent having the formula:

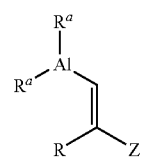

wherein each $R^a$ is independently selected from lower alkyl and cycloalkyl; R is a member selected from vinyl, allyl, 2-buten-1-yl and 3-trimethylsilylprop-2-yn-1-yl; and Z is a member selected from the group consisting of $CH_3$ and $CF_3$; to provide a compound having the formula:

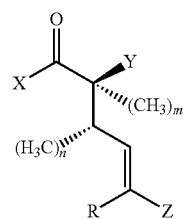

wherein the subscripts n and m are each independently 0 or 1, indicating the absence or presence of methyl groups at the respective positions; X is a member selected from $CH_3$, $OR^1$, $N(R^2)_2$ and $N(R^2)OR^1$; wherein $R^1$ is selected from H, lower alkyl, a carboxylic acid protecting group and a hydroxy protecting group, and each $R^2$ is independently selected from H, lower alkyl and an amino protecting group; Y is a member selected from $OR^3$ and $NHR^4$, wherein $R^3$ is selected from H, lower alkyl and a hydroxy protecting group, and $R^4$ is selected from H, lower alkyl and an amino protecting group; Z is a member selected from $CH_3$ and $CF_3$; and R is selected from vinyl, allyl, 2-buten-1-yl and 3-trimethylsilylprop-2-yn-1-yl.

In a related aspect, the present invention provides a method for the preparation of an epothilone intermediate, comprising:

a) contacting a compound having the formula:

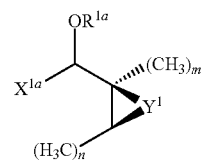

wherein the subscripts n and m are each independently 0 or 1, indicating the absence or presence of methyl groups at the respective positions; $X^{1a}$ is a member selected from H and $CH_3$; $R^{1a}$ is selected from lower alkyl and a hydroxy protecting group, and; $Y^1$ is a member selected from O and $NR^4$, wherein $R^4$ is selected from H, lower alkyl and an amino protecting group;

with an alane reagent having the formula:

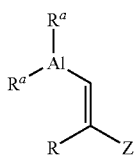

wherein each $R^a$ is independently selected from lower alkyl and cycloalkyl; R is a member selected from vinyl, allyl, 2-buten-1-yl and 3-trimethylsilylprop-2-yn-1-yl; and Z is a member selected from $CH_3$ and $CF_3$;
to provide a compound having the formula:

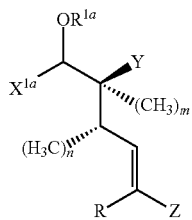

wherein the subscripts n and m are each independently 0 or 1, indicating the absence or presence of methyl groups at the respective positions; $X^{1a}$ is a member selected from H and $CH_3$; $R^{1a}$ is a member selected from lower alkyl and a hydroxy protecting group; Y is a member selected from $OR^3$ and $NHR^4$, wherein $R^3$ is selected from H, lower alkyl and a hydroxy protecting group, and $R^4$ is selected from H, lower alkyl and an amino protecting group; Z is a member selected from $CH_3$ and $CF_3$; and R is selected from vinyl, allyl, 2-buten-1-yl and 3-trimethylsilylprop-2-yn-1-yl.

The present invention further provides methods of converting the intermediates above to epothilone compounds.

DETAILED DESCRIPTION OF THE INVENTION

Figure 1:
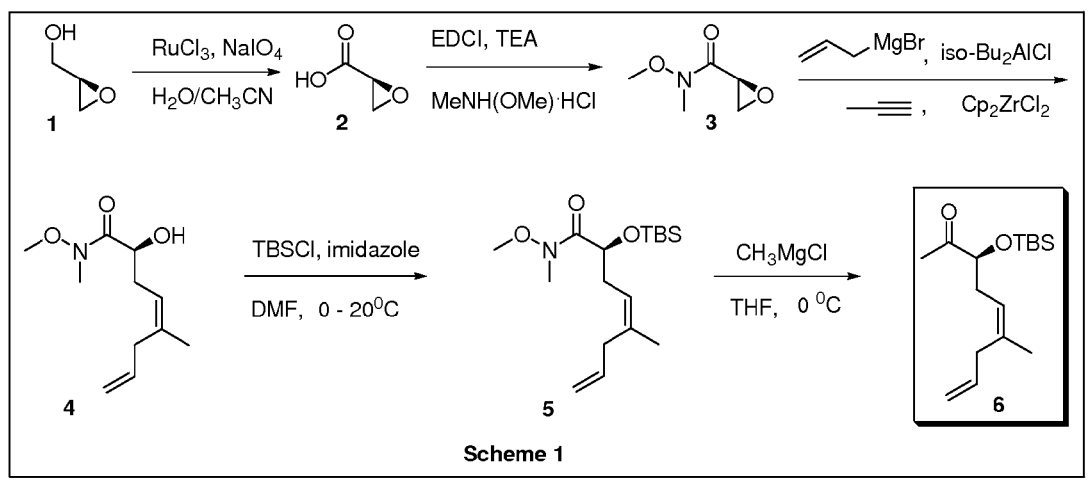
FIG. 1 illustrates the preparation of an alane reagent of the invention.

The present invention provides compounds and synthetic methods useful in the preparation of epothilones. By "epothilones" is meant a compound of general structure

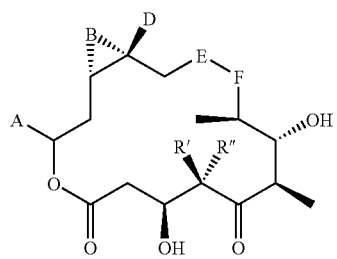

wherein A is aryl, heteroaryl, arylalkenyl, or heteroarylalkenyl; B is —O— or a bond; D is H or unsubstituted or substituted lower alkyl; E-F is C=C or $CH_2$—$CH_2$; and R' and R" are independently H, lower alkyl or lower haloalkyl. These compounds include the naturally-occurring epothilones known in the art, for example those described in Hardt et al., "New Natural Epothilones from *Sorangium cellulosum*, Strains So ce90/B2 and So ce90/D13: Isolation, Structure Elucidation, and SAR Studies," *J. Natural Products* 64: 847-56 (2001), as well as synthetic derivatives and analogs thereof, for example epothilone analogs having a 9,10-alkene such as those described in Rivkin et al., "Discovery of (E)-9,10-dehydroepothilones through Chemical Synthesis: On the Emergence of 26-Trifluoro-(E)-9,10-dehydro-12,13-desoxyepothilone B as a Promising Anticancer Drug Candidate," *J. Am. Chem. Soc.* 126: 10913-10922 (2004), each of which is incorporated herein by reference.

Definitions

As used herein, the term "alkyl" refers to a straight or branched, saturated aliphatic radical containing one to ten carbon atoms, unless otherwise indicated e.g., alkyl includes methyl, ethyl, propyl, isopropyl, butyl, sec-butyl, isobutyl, tert-butyl, and the like. The term "lower alkyl" refers to an alkyl radical having from one to four carbon atoms.

The term "aryl" refers to a monocyclic or fused bicyclic ring assembly containing 6 to 10 ring carbon atoms wherein each ring is aromatic e.g., phenyl or naphthyl.

The term "arylalkenyl" refers to a group —$R^xR^y$ wherein $R^y$ is an aryl group and $R^x$ is an alkenyl group wherein the alkenyl portion has from two to six carbon atoms and from one to three double bonds. Examples of arylalkenyl groups are styryl, 1-phenylpropen-2-yl, 3-phenyl-propen-1-yl, and the like.

The term "heteroaryl" refers to a monocyclic or fused bicyclic ring assembly containing 6 to 10 ring atoms wherein each ring is aromatic and at least one of the ring atoms is a heteroatom (N, O, S). Examples of heteroaryl groups are pyridyl, pyrimidinyl, thienyl, furanyl, thiazolyl, pyrazolyl, oxazolyl, quinolinyl, quinazolinyl, benzofuranyl, benzothiazolyl, benzimidazolyl, and the like.

The term "heteroarylalkenyl" refers to a group —$R^xR^y$ wherein $R^y$ is a heteroaryl group and $R^x$ is an alkenyl group wherein the alkenyl portion has from two to six carbon atoms and from one to three double bonds. Examples of heteroarylalkenyl groups are 1-(thiazol-2-yl)ethenyl, 2-(thiazol-2-yl) ethenyl, 2-(2-pyridyl)propen-1-yl, and the like.

The term "substituted" refers to an additional substituent group selected from halogen (preferably fluoro, chloro, or bromo), hydroxy, amino, mercapto, and the like. Preferred substituents for the groups described herein as substituted lower alkyl or substituted alkyl are halogens, particularly fluoro substituents.

The term "substantially free of its enantiomeric or diastereomeric forms" refers to a compound that is obtained or isolated in a form that is contaminated by no more than 10% of an enantiomeric or diastereomeric form of the compound. In most instances, the compound will be isolated in a form that is contaminated by no more than 5%, 4%, 3%, 2%, 1%, 0.5% or 0.25% of an enantiomeric or diastereomeric form of the compound.

The term "carboxylic acid protecting group" refers to a protecting group for the —COOH moiety. Examples of suitable carboxylic acid protecting groups can be found in, for example, Greene and Wuts, PROTECTIVE GROUPS IN ORGANIC SYNTHESIS, 3rd edition, John Wiley & Sons, New York, N.Y. (1999).

The term "hydroxy protecting group" refers to a protecting group for the —OH moiety when the —OH would otherwise be attached to an alkyl, aryl or amine group. Examples of suitable hydroxy protecting groups can be found in, for example, Greene and Wuts, ibid.

The term "amino protecting group" refers to a protecting group for the amino moiety. In this instance, the amino group can be attached to an alkyl or aryl moiety or can be present as part of an amide or hydroxamide functional group. Examples of suitable amino protecting groups can be found in, for example, Greene and Wuts, ibid.

Embodiments of the Invention

The present invention resides in a number of synthetic intermediates and processes for preparing those intermediates as exemplified in FIG. 1. New reagents for use in the synthetic processes are also provided.

Reagents for the Preparation of Epothilones

Turning first to the novel reagents, the present invention provides in one aspect, alane reagents that are useful in the preparation of epothilones, the reagents comprising a compound having the formula:

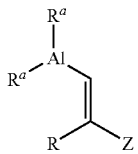

wherein each $R^a$ is independently selected from lower alkyl and cycloalkyl; R is a member selected from vinyl, allyl, 2-buten-1-yl and 3-trimethylsilylprop-2-yn-1-yl; and Z is a member selected from $CH_3$ and $CF_3$. Typically, the reagents will further comprise an aprotic solvent that facilitates the storage and handling of the alane compound. Suitable aprotic solvents include hexane, heptane, dichloromethane, 1,2-dichloroethane and ethers such as ethyl ether and methyl tert-butyl ether. In some embodiments, the alane reagent comprising an alane compound of the formula above and a suitable aprotic solvent is packaged and titrated to a known molar concentration so that volumetric measurement of the alane compound can be readily made. In other embodiments, the alane reagent is prepared immediately prior to use.

In one group of embodiments, each $R^a$ is independently selected from lower alkyl, more preferably, methyl, ethyl, n-propyl, and isopropyl, and cyclopropyl; R is a member selected from vinyl, allyl, 2-buten-1-yl and 3-trimethylsilylprop-2-yn-1-yl; and Z is $CH_3$. In other embodiments, each $R^a$ is independently selected from lower alkyl, more preferably, methyl, ethyl, n-propyl, and isopropyl; R is selected from allyl, 2-buten-1-yl and 3-trimethylsilylprop-2-yn-1-yl; and Z is $CH_3$. In one group of particularly preferred embodiments, each $R^a$ is methyl.

The alane reagents of the present invention are conveniently prepared from commercially available $(R^a)_2AlCl$. In some embodiments, the alane reagents of the present invention are prepared by contacting $(R^a)_2AlCl$ with a suitable Grignard reagent (allylmagnesium bromide), then adding $Cp_2ZrCl_2$ to the intermediate reagent. As indicated in the examples below, the dialkylaluminum chloride reagent and the Grignard reagent, typically in a solvent such as diethyl ether, are combined in an inert atmosphere (e.g., $N_2$ or argon) at a reduced temperature (e.g., 0° C. to −30° C. or lower), then warmed to room temperature. After removal of solvent and addition of a hydrocarbon solvent such as hexane or a mixture of isomeric hexanes (anhydrous), $Cp_2ZrCl_2$ is added to the intermediate reagent along with an alkyne, for example, propyne or 3,3,3-trifluoropropyne. See FIG. 1.

Intermediates in the Preparation of Epothilones

As noted above, the present invention provides, in another aspect, compounds useful as intermediates in the preparation of epothilones, the compounds having the formula:

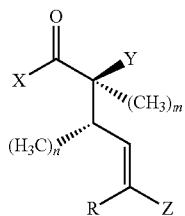

wherein the subscripts n and m are each independently 0 or 1, indicating the absence or presence of methyl groups at the respective positions. The letter X represents a member selected from $CH_3$, $OR^1$, $NHR^2$ and $N(R^2)OR^1$; wherein $R^1$ is selected from H, lower alkyl, a carboxylic acid protecting group and a hydroxy protecting group, and $R^2$ is selected from H, lower alkyl and an amino protecting group. The letter Y represents a member selected from $OR^3$ and $N(R^4)_2$, wherein $R^3$ is selected from H, lower alkyl and a hydroxy protecting group, and each $R^4$ is independently selected from H, lower alkyl and an amino protecting group. The letter Z represents a member selected from $CH_3$ and $CF_3$. The letter R represents a member selected from vinyl, allyl, 2-buten-1-yl and 3-trimethylsilylprop-2-yn-1-yl. In the compounds above, (a) when X is $CH_3$, Y is other than OH;
(b) when X is $N(CH_3)OCH_3$, and Z is $CF_3$, then Y is other than OH; and
(c) when X is $N(CH_3)OCH_3$, and Z is $CH_3$, then Y is other than O—Si(Et)$_3$.

Additionally, the compounds above are substantially free of their enantiomeric or diastereomeric forms.

In one group of embodiments, X is $N(R^2)OR^1$. Within this group of embodiments, preferably Y is $N(R^4)_2$. Still further preferred are those embodiments in which X is $N(CH_3)(OCH_3)$ and Y is $NHR^4$, wherein $R^4$ is H or an amino protecting group.

In another group of embodiments, X is $CH_3$. Within this group of embodiments, preferably Y is $N(R^4)_2$.

In yet another group of embodiments, X is $OR^1$. Within this group of embodiments, Y is preferably $OR^3$. Still further preferred are those embodiments in which X is selected from $OCH_3$ and $OCH_2CH_3$; and Y is $OR^3$ wherein $R^3$ is selected from H and a hydroxy protecting group.

The compounds described as intermediates are conveniently prepared as described in the methods below and in the examples.

Methods for the Preparation of Epothilone Intermediates

In yet another aspect, the present invention provides a method for the preparation of epothilone intermediates, the method comprising:

a) contacting a compound having the formula:

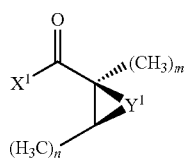

wherein the subscripts n and m are each independently 0 or 1, indicating the absence or presence of methyl groups at the respective positions; $X^1$ is a member selected from $OR^1$, $N(R^2)_2$ and $N(R^2)OR^1$; wherein $R^1$ is selected from H, lower alkyl, a carboxylic acid protecting group and a hydroxy protecting group, and each $R^2$ is independently selected from H, lower alkyl and an amino protecting group; $Y^1$ is a member selected from O and $NR^4$, wherein $R^4$ is selected from the group consisting of H, lower alkyl and an amino protecting group; with an alane reagent having the formula:

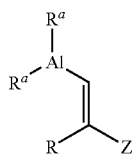

wherein each $R^a$ is independently selected from lower alkyl and cycloalkyl; R is a member selected from vinyl, allyl, 2-buten-1-yl and 3-trimethylsilylprop-2-yn-1-yl; and Z is a member selected from the group consisting of $CH_3$ and $CF_3$; to provide a compound having the formula:

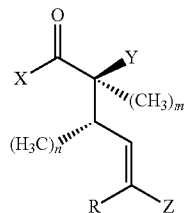

wherein the subscripts n and m are each independently 0 or 1, indicating the absence or presence of methyl groups at the respective positions; X is a member selected from $CH_3$, $OR^1$, $N(R^2)_2$ and $N(R^2)OR^1$; wherein $R^1$ is selected from H, lower alkyl, a carboxylic acid protecting group and a hydroxy protecting group, and each $R^2$ is independently selected from H, lower alkyl and an amino protecting group; Y is a member selected from $OR^3$ and $NHR^4$, wherein $R^3$ is selected from H, lower alkyl and a hydroxy protecting group, and $R^4$ is selected from H, lower alkyl and an amino protecting group; Z is a member selected from $CH_3$ and $CF_3$; and R is selected from vinyl, allyl, 2-buten-1-yl and 3-trimethylsilylprop-2-yn-1-yl.

In the method above, the starting compound can be prepared according to literature methods (see, Davis et al., *J. Org. Chem.*, 1999, 64, 7559-7567; and Claudio Paloma et al, *J. Org. Chem.*, 2000, 65, 9007-9012), or in some embodiments, is commercially available (for example, (+)-(R)-glycidol). For those embodiments in which the starting materials is prepared according to literature methods, the starting compound is preferably purified prior to reaction with the alane reagent. In some embodiments, the starting compound can be freshly prepared in a solvent and contacted with the alane reagent in a solvent that is the same or different from the solvent used with the starting material. Typically, the alane reagent used will be prepared in situ as noted above.

Conditions for the contacting are varied and will depend on the nature of the starting material and the alane reagent that is used. Generally, the contacting takes place in a solvent such as an ether (e.g., THF, diethylether), hydrocarbon (e.g., heptane or toluene) or chlorinated hydrocarbon (e.g., methylene chloride or 1,2-dichloroethane). In preferred embodiments, the solvent is 1,2-dichloroethane. Additionally, the contacting preferably takes place at reduced temperatures of from −78° C. to about 0° C.; more preferably at about −43° C. to about −20° C.

Following the initial contacting, preferably at a temperature of from −78° C. to about 0° C., the reaction mixture is warmed to a temperature of from 5° C. to about 15° C. over a period of 30 min to about 10 hours. In some preferred embodiments, the reaction mixture is warmed to a temperature of from 5° C. to about 15° C. over a period of 1 hour to about 5 hours.

The reaction is typically quenched by careful addition of the reaction mixture to a mixture of an organic solvent (e.g., ethyl acetate) and water, containing a weak acid (e.g., citric acid), while keeping the temperature of the mixture below about 50° C. The remaining workup steps are standard and can be modified according to the reactants used, as well as the product. Generally, the organic layer of the quenched mixture is drawn off. The aqueous layer is extracted with additional amounts of the organic solvent, and the combined organic solvent portions are washed (using, for example, brine, saturated sodium bicarbonate and the like), dried over an anhydrous drying agent (for example, magnesium sulfate or sodium sulfate), filtered and concentrated.

In some embodiments, additional steps can be used and include:

(b) adding a protecting group to convert Y=OH to Y=O-hydroxy protecting group; and (c) transforming the compound wherein X is $OR^1$, $NHR^2$ or $N(R^2)OR^1$ to a compound wherein X is $CH_3$.

In a related aspect, the present invention provides a method for the preparation of an epothilone intermediate, comprising:

a) contacting a compound having the formula:

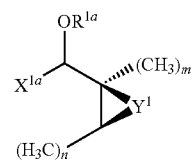

wherein the subscripts n and m are each independently 0 or 1, indicating the absence or presence of methyl groups at the respective positions; $X^{1a}$ is a member selected from H and $CH_3$; $R^{1a}$ is selected from lower alkyl and a hydroxy protecting group, and; $Y^1$ is a member selected from O and $NR^4$, wherein $R^4$ is selected from H, lower alkyl and an amino protecting group;

with an alane reagent having the formula:

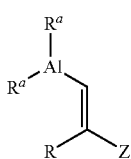

wherein each R[a] is independently selected from lower alkyl and cycloalkyl; R is a member selected from vinyl, allyl, 2-buten-1-yl and 3-trimethylsilylprop-2-yn-1-yl; and Z is a member selected from $CH_3$ and $CF_3$;

to provide a compound having the formula:

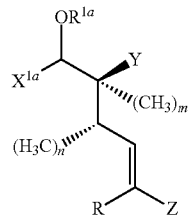

wherein the subscripts n and m are each independently 0 or 1, indicating the absence or presence of methyl groups at the respective positions; $X^{1a}$ is a member selected from H and $CH_3$; $R^{1a}$ is a member selected from lower alkyl and a hydroxy protecting group; Y is a member selected from $OR^3$ and $NHR^4$, wherein $R^3$ is selected from H, lower alkyl and a hydroxy protecting group, and $R^4$ is selected from H, lower alkyl and an amino protecting group; Z is a member selected from $CH_3$ and $CF_3$; and R is selected from vinyl, allyl, 2-buten-1-yl and 3-trimethylsilylprop-2-yn-1-yl.

The present invention further provides methods of converting the intermediates above to epothilone compounds.

EXAMPLES

In the examples below, the following abbreviations are used: DMAP, 4-dimethylaminopyridine; EtOAc, ethyl acetate; EDCl, 1,2-dichloroethane or ethylenedichloride; TEA, triethylamine; DMF, dimethylformamide; TBSCl, t-butyldimethylsilylchloride; TBS; THF, tetrahydrofuran; $Et_2O$, diethylether; TLC, thin layer chromatography; mol, moles; mmol, millimoles; mL, milliliters.

Example 1

This example illustrates the synthesis of (S,Z)-3-((tert-butyl)dimethylsiloxy)-6-methylnona-5,8-dien-2-one (Scheme 1).

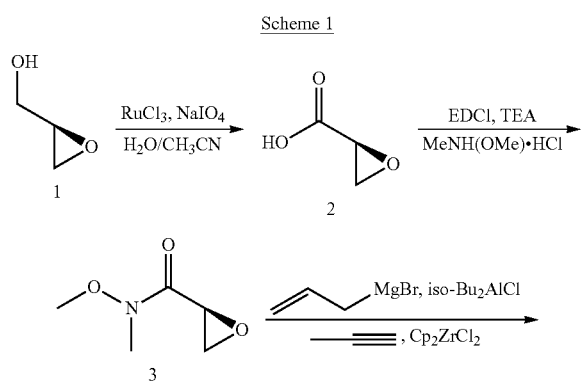

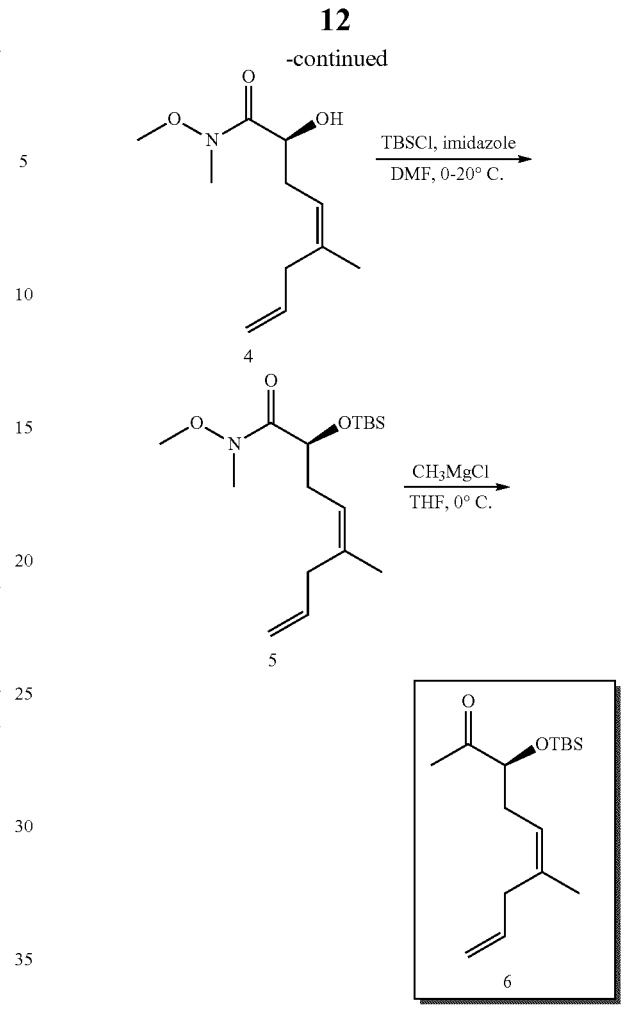

Step 1: (S)-oxirane-2-carboxylic acid (2)

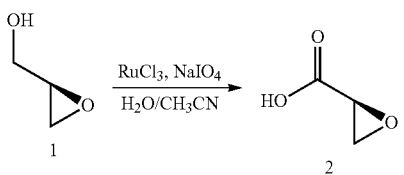 [SMILES: OC[C@@H]1CO1 ; O=C(O)[C@@H]1CO1]

To a solution of (+)-(R)-Glycidol 1 (60.0 g, 0.810 mol, 1.0 equiv.) in $CH_3CN$ (1400 mL) was added $H_2O$ (36.5 mL, 2.025 mol, 2.5 equiv.) and $NaIO_4$ (520 g, 2.43 mol, 3.0 equiv.), followed by addition of $RuCl_3$ (1.68 g, 8.1 mmol, 0.01 equiv.). The reaction mixture was stirred at room temperature for 3 hours to obtain a green suspension. More $H_2O$ (36.5 mL, 2.025 mol, 2.5 equiv.) was added at 0° C., and the stirring was continued for 4 hours at 0° C. (ice bath) and 8 hours at room temperature (water bath). To the reaction mixture was added $Et_2O$ (800 mL) and the resultant suspension was filtered through a pad of silica gel (2 cm thick of silica gel in a 3 L filtration funnel) and washed with $Et_2O$ (3×200 mL). The solvent was removed under reduced pressure and the residue was dissolved in $Et_2O$ (400 mL). The $Et_2O$ solution was filtered through a pad of silica gel (2 cm thick of silica gel in a 600 ml filtration funnel) and washed with $Et_2O$ (8×100 mL).

The solvent was removed under reduced pressure to obtain the crude product 2 (72.1 g) as light-yellow oil, which was used immediately in the next step without further purification.

Step 2:
(S)—N-methoxy-N-methyloxirane-2-carboxamide
(3)

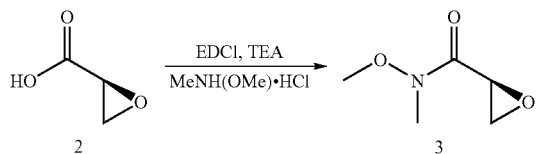

To a solution of the crude acid 2 (~72.0 g, ~0.810 mol, 1.0 equiv.) in $CH_2Cl_2$ (1600 mL) was added $NEt_3$ (120 mL, 0.859 mol, 1.06 equiv.), DMAP (92 mg, 0.00082 mol, 0.001 equiv.) and O,N-Dimethyl-hydroxylamine hydrochloride (95.74 g, 0.982 mol, 1.21 equiv.) at 0° C. The resultant mixture was stirred for 10 minutes at −5° C. and EDCI (198.5 g, 1.035 mol, 1.27 equiv.) was added. The reaction mixture was stirred for 4 hours at 0° C. and diluted with hexanes (800 mL). The mixture was filtered through a pad of silica gel (2 cm thick of silica gel in a 3 L filtration funnel) and washed with $Et_2O$ (10×300 mL). The solvent was removed under reduced pressure to afford the crude amide 3 (92.2 g, 0.709 mmol, 87.5% for two steps) as slight-yellow oil. This crude product was dissolved in 1,2-dichloroethane (200 mL) and dried over molecular sieves at −20° C. for 2 hours before used in the next step).

Step 3: (S,Z)-2-hydroxy-N-methoxy-N,5-dimethy-locta-4,7-dienamide (4)

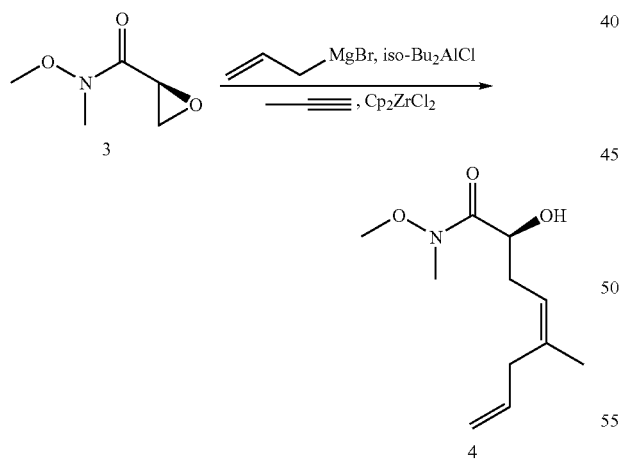

Under the protection of nitrogen, to a solution of allyl magnesium bromide (1517 mL, 1.517 mol, 1.0 M in $Et_{2O}$, 1.0 equiv.) was added neat isobutylaluminium chloride (268 g, 1.517 mol, 1.0 equiv.) during a period of 1 hour at 0° C. The reaction mixture was stirred for 4 hours at room temperature, and settled for 6 hours. The clear upper layer was transfer from the reaction flask (flask No. 1) to another dry flask (flask No. 2) through a cannula. The solvent in flask No. 2 was removed with an air-free adapter under reduced pressure. To the flask No. 1 was added anhydrous hexanes (300 mL), stirred for 5 minutes, settled for 20 minutes and the clear solution was transfer to flask No. 2 through cannula. This extraction with hexanes was repeated for 3 times and the solution in flask No. 2 was concentrated to about 480 g. Anhydrous hexanes (400 mL) was added to the residue and concentrated, and then the presumably $Et_2O$ free solution was diluted with hexanes (600 mL). The upper clear hexanes solution was transferred to a dry flask (flask No. 3) under nitrogen and the remained white precipitate was extracted with hexanes (2×200 mL). The combined hexanes solution in flask No. 3 was concentrated to about 430 g and dissolved in anhydrous $ClCH_2CH_2Cl$ (800 mL). The resultant solution was then cooled to −15° C. To this cooled solution was added propyne (75 g, 1.874 mol, 1.235 equiv.), $Cp_2ZrCl_2$ (88.7 g, 0.303 mol, 0.2 equiv., one portion) and $H_2O$ (0.137 g, 0.0076 mol, 0.005 equiv., dropwise). The reaction mixture was warm up to room temperature and stirred for 14 hours to obtain a brownish red solution, which was then placed in a −43° C. bath (−20° C. is fine, the yield will be reduced only slightly). To this cooled solution was added compound 3 (125.0 g, 0.9608 mol, 0.641 equiv.) in 1,2-dichloroethane (200 mL). The reaction mixture was warmed up to 10° C. in 3 hours and then added slowly to a stirring mixture of citric acid (1200 g), EtOAc (2000 mL) and $H_2O$ (1200 mL) (with internal temperature controlled under 40° C. using ice bath). The aqueous phase was extracted with EtOAc (2×300 mL). The combined organic solution was washed with brine (200 mL), saturated $NaHCO_3$ (200 mL) and brine (200 mL). The organic solution was then dried over anhydrous $MgSO_4$, filtered through a thin pad of silica gel and concentrated. The residue was purified with column chromatography (0% EtOAc in hexane to 50%) to provide the desired product 4 (128.1 g, 0.601 mol, 62.5%) as colorless oil.

Note: Later study found that filtration of the allylaluminum solution through a funnel under nitrogen may significantly simplify the tedious hexanes extraction procedures.

Step 4: (S,Z)-2-((tert-butyl)dimethylsiloxy)-N-methoxy-N,5-dimethylocta-4,7-dienamide (5)

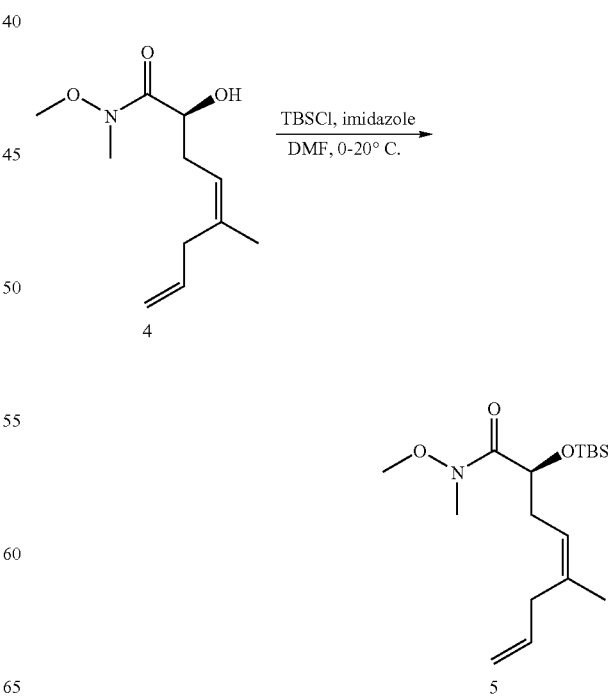

To an anhydrous DMF (250 mL) solution of the alcohol 4 (70.7 g, 329 mmol) was added tert-butyldimethylsilyl chloride (TBSCl, 55 g, 364 mmol) and imidazole (30 g, 441 mmol) at 0° C. The reaction was allowed to warm to room temperature, and was stirred overnight. The reaction progress was followed by TLC (5:1/hexanes:ethyl acetate). The reaction mixture was poured to a 4 L separation funnel containing diethyl ether (1.7 L), and was separated. The organics were washed with water (4×500 mL) and brine (1×250 mL), dried over magnesium sulfate. Filtration and evaporation under vacuum afforded the crude product 5 as yellowish oil (107 g, 99%), which was used directly for the next step without further purification.

Step 5: (S,Z)-3-((tert-butyl)dimethylsiloxy)-6-methylnona-5,8-dien-2-one (6)

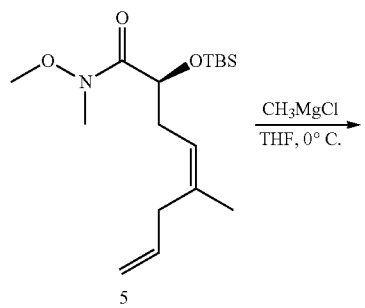

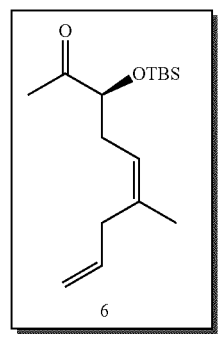

To a THF (300 mL) solution of the starting material 5 (152.6 g, 465 mmol) was slowly added methylmagnesium chloride (200 mL, 3.0 M in THF, 600 mmol) in 30 min at 0° C. The reaction was stirred over 30 min at 0° C., and was carefully quenched with saturated ammonium chloride water solution (300 mL). Its pH was then adjusted to 7 with 1N hydrochloric acid. Volatiles were removed via a rotavap. The residue was extracted with diethyl ether (1 L). Ethereal extracts were washed with water and brine, dried over magnesium sulfate. Flash chromatography on silica gel (0-3% ethyl acetate in hexanes) afforded the desired product 6 as pale yellow oil (125 g, 95%).

Example 2

This example illustrates additional epoxide ring openings with alkenyl diisobutylaluminum reagents, using the conditions noted and following the procedures outlined above. The results are provided in Table 1.

TABLE 1

The ring-opening alkenylation of epoxides

| Entry | Epoxide | Temperature | Reaction time (hr) | Products | Yield |
|---|---|---|---|---|---|
| 1 | 6a | −30° C. | 0.5 | 7a | 53% |
| 2 | 6b | −30° C. | 0.5 | 7b | 62% |
| 3 | 6c | −30° C. | 0.5 | 7c | 64% |

TABLE 1-continued

The ring-opening alkenylation of epoxides

| Entry | Epoxide | Temperature | Reaction time (hr) | Products | Yield |
|---|---|---|---|---|---|
| 4 | 6d (OBn epoxide) | −10° C. | 2 | 7d | |
| 5 | 6e (OTBS epoxide) | 20° C. | 10 | 7e | 35% |

All results were obtained with the application of 1.5 equiv. of alkenyl diisobutylaluminum; the solvent was ClCH$_2$CH$_2$Cl. Epoxides with carbonyl groups at a position (entry 1, 2 and 3) showed high reactivity with the alkenyl diisobutylaluminum, and were consumed completely at −30° C. in 0.5 hour. The NMR of the crude products indicated that there was only very small amount isomers (usually <4%) formed. The reactions were slower when the carbonyl group was replaced with an ethereal group at a position (entry 4 and 5). Epoxides with the more bulky OTBS group (entry 4) were also more slow to complete reaction than the epoxide with OBn group (entry 5).

Example 3

Figure 2:
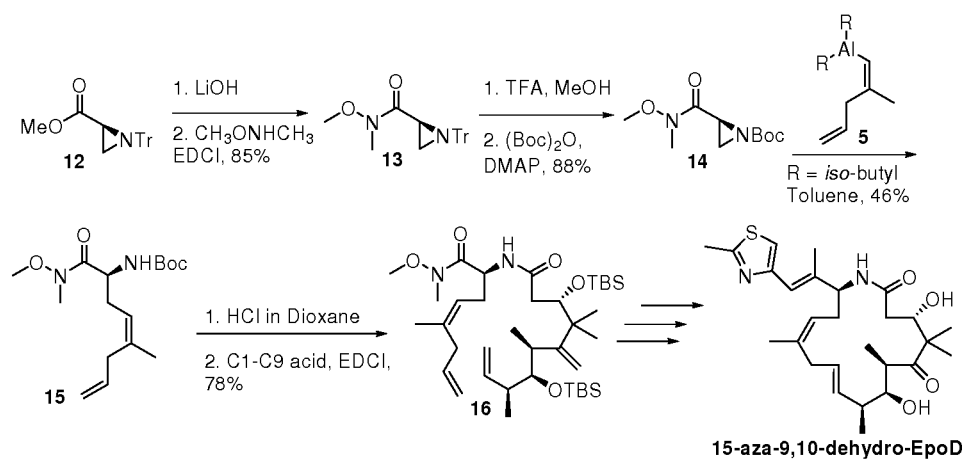
FIG. 2 provides a reaction scheme illustrating the opening of a protected aziridine with an alane reagent, followed by attachment of the C1-C9 acid fragment and conversion to 15-aza-9,10-dehydro-Epo D.

This example illustrates an aziridine ring opening with an alkenyl diisobutylaluminum reagents (see FIG. 2).

Started from commercially available compound 12, the hydrolysis followed by coupling reaction provided compound 13 (using conditions as described above). The Tr protection group was removed with TFA and the free amine was protected with a Boc group. The aziridine opening reaction with the indicted alane reagent afforded the Boc protected amine 15, which was converted to 15-aza-9,10-dehydro-epoD.

All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A method for the preparation of an epothilone intermediate, said method comprising:

a) contacting a compound having the formula:

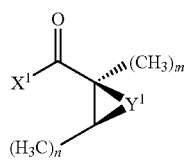

wherein the subscripts n and m are each independently 0 or 1, indicating the absence or presence of methyl groups at the respective positions;

$X^1$ is a member selected from the group consisting of $OR^1$, $N(R^2)_2$ and $N(R^2)OR^1$; wherein $R^1$ is selected from the group consisting of H, lower alkyl, a carboxylic acid protecting group and a hydroxy protecting group, and each $R^2$ is independently selected from the group consisting of H, lower alkyl and an amino protecting group;

$Y^1$ is a member selected from the group consisting of O and $NR^4$, wherein $R^4$ is selected from the group consisting of H, lower alkyl and an amino protecting group;

with an alane reagent having the formula:

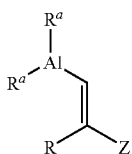

wherein each $R^a$ is independently selected from lower alkyl and cycloalkyl;

R is a member selected from the group consisting of vinyl, allyl, 2-buten-1-yl and 3-trimethylsilylprop-2-yn-1-yl; and Z is a member selected from the group consisting of $CH_3$ and $CF_3$;
to provide a compound having the formula:

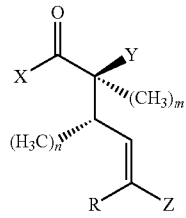

wherein the subscripts n and m are each independently 0 or 1, indicating the absence or presence of methyl groups at the respective positions;

X is a member selected from the group consisting of $CH_3$, $OR^1$, $N(R^2)_2$ and $N(R^2)OR^1$; wherein $R^1$ is selected from the group consisting of H, lower alkyl, a carboxylic acid protecting group and a hydroxy protecting group, and each $R^2$ is independently selected from the group consisting of H, lower alkyl and an amino protecting group;

Y is a member selected from the group consisting of $OR^3$ and $NHR^4$, wherein $R^3$ is selected from the group consisting of H, lower alkyl and a hydroxy protecting group, and $R^4$ is selected from the group consisting of H, lower alkyl and an amino protecting group;

Z is a member selected from the group consisting of $CH_3$ and $CF_3$; and

R is selected from the group consisting of vinyl, allyl, 2-buten-1-yl and 3-trimethylsilylprop-2-yn-1-yl.

2. A method in accordance with claim 1, wherein said alane reagent is prepared in situ.

3. A method in accordance with claim 2, wherein said alane reagent is prepared from propyne, and a dialkyl allylaluminum.

4. A method in accordance with claim 3, wherein said dialkyl allylaluminum is prepared from an allyl magnesium reagent and a dialkylaluminum halide.

* * * * *